(12) United States Patent
Cailleteau (10) Patent No.: US 9,592,170 B2
(45) Date of Patent: Mar. 14, 2017

(54) FLEXIBLE POUCH HAVING AN OPENING SLEEVE

(71) Applicant: M3AT SA, Botterens (CH)

(72) Inventor: Benoît Cailleteau, Marseilles (FR)

(73) Assignee: M3AT SA, Botterens (CH)

( * ) Notice: Subject to any disclaimer, the term of this patent is extended or adjusted under 35 U.S.C. 154(b) by 180 days.

(21) Appl. No.: 14/425,705

(22) PCT Filed: Aug. 27, 2013

(86) PCT No.: PCT/EP2013/067712
§ 371 (c)(1),
(2) Date: Mar. 4, 2015

(87) PCT Pub. No.: WO2014/037246
PCT Pub. Date: Mar. 13, 2014

(65) Prior Publication Data
US 2015/0216754 A1    Aug. 6, 2015

(30) Foreign Application Priority Data

Sep. 7, 2012  (FR) ...................................... 12 58388

(51) Int. Cl.
| | | |
|---|---|---|
| *A47K 11/00* | (2006.01) | |
| *A61G 9/00* | (2006.01) | |
| *A61F 5/44* | (2006.01) | |
| *B65D 33/16* | (2006.01) | |

(52) U.S. Cl.
CPC ................ *A61G 9/006* (2013.01); *A61F 5/44* (2013.01); *A61F 5/4407* (2013.01); *B65D 33/16* (2013.01)

(58) Field of Classification Search
CPC ....... A61F 5/453; A61F 5/4556; A61G 9/006; B65D 33/007
USPC ...... 383/33; 4/114.1, 144.1–144.4, 451, 454, 4/484; 604/346, 349–353
See application file for complete search history.

(56) References Cited

U.S. PATENT DOCUMENTS

| 3,403,410 A | * | 10/1968 | Benzel | ...................... A61F 5/44 4/144.2 |
|---|---|---|---|---|
| 5,065,459 A | | 11/1991 | Tjahaja et al. | |
| 5,745,926 A | * | 5/1998 | Cailleteau | ................. A61F 5/44 383/44 |
| 5,946,738 A | * | 9/1999 | Cailleteau | ............. A61F 5/4404 4/144.1 |

(Continued)

FOREIGN PATENT DOCUMENTS

| EP | 0847742 A1 | 6/1998 |
|---|---|---|
| FR | 2759981 A1 | 8/1998 |

*Primary Examiner* — Paul R Durand
*Assistant Examiner* — Nicholas Ros
(74) *Attorney, Agent, or Firm* — MH2 Technology Law Group, LLP (57) ABSTRACT

The pouch comprises a flexible bag (12) having an opening (12A) with its edge fastened to two opposite walls of a reinforcing sleeve (18) that projects to the outside of the bag. The pouch can adopt a flat configuration in which the walls of the sleeve are situated one against the other, and a utilization configuration in which the walls form a channel that holds the opening open. The first wall (20A) of the sleeve (18) presents a first longitudinal end strip (30A), while the second wall presents a sliding edge (32B) suitable for sliding against the inside face of the first longitudinal strip on the pouch passing from its flat configuration to its utilization configuration.

14 Claims, 4 Drawing Sheets

(56) References Cited

U.S. PATENT DOCUMENTS 6,345,911 B1 2/2002 Young et al.
2012/0222208 A1\* 9/2012 Jacobson ............. A61F 5/4556
4/484

\* cited by examiner

FLEXIBLE POUCH HAVING AN OPENING SLEEVE

The present invention relates to a pouch comprising a flexible bag having an opening with its edge fastened to two opposite walls of a reinforcing sleeve projecting to the outside of the bag, the pouch being suitable for adopting a flat configuration in which said walls are situated one against the other, and a utilization configuration in which the walls form a channel that holds the opening open.

Pouches of this type are known, e.g. from European patent application No. 0 847 742. They are used to receive substances, generally in liquid form, in particular waste of human or animal origin, such as urine. These pouches are stored while in their flat configuration. In order to use them, the sleeve is manipulated so that its walls form the channel that holds the opening open, thus putting the pouch into its utilization configuration, allowing waste to be poured into the inside of the pouch. Once the waste has been introduced therein, it suffices to release the sleeve to allow the pouch to return towards its flat configuration.

Such pouches are commonly made out of thin sheets of plastics material or other materials, possibly transparent materials, and having sufficient flexibility. In order to open a pouch, the manipulation of the sleeve consists in deforming its walls so as to constrain them to adopt a convex shape (seen from outside the pouch) in which they form between them the channel that holds the opening open.

The transverse dimensions of the opening are selected appropriately for the use that is to be made of the pouch. Generally, in particular when the pouch is for receiving urine, the sleeve needs to be suitable for being manipulated in one hand only, and its transverse dimensions are then generally considerably smaller than the transverse dimensions of the main portion of the pouch.

European patent application No. 0 847 742 is directed to ensuring that the manipulation of the sleeve so as to cause it to take up the channel shape leads to the walls of the bag moving apart not only at the edges of the opening of the bag, but also downstream from the opening so as to ensure that the substance introduced into the pouch does not have any tendency to reflux, i.e. to flow back out. For this purpose, the sleeve is provided with internal spreader tabs. This gives great freedom of choice concerning the material used for making the bag of the pouch. The invention constituting the subject matter of the above-mentioned European patent application ensures that the sheets forming the bag move apart even if they are very flexible, and even if they initially have a tendency to remain slightly stuck together.

Another problem that arises in preparing a pouch of the above-specified type is that of ensuring that substances (and in particular waste such as urine) are conveyed effectively to the inside of the bag. When the pouch is used as a urine pouch for male use, this does not usually lead to any particular difficulty providing the users' penis is inserted far enough through the opening (in the channel formed by the sleeve). Likewise, for any waste-collection application in which the waste is introduced into the pouch from a projecting endpiece or member that can be inserted into the pouch through the opening over a length that is sufficient, conveying the substances into the inside of the pouch does not present any difficulty.

In contrast, difficulties exist when it is desired to use pouches in other applications where the member from which the substances flow is not of a type suitable for being introduced over a sufficient length into the channel formed by the sleeve. This applies for example with pouches that are used as urine pouches for female use. Under such circumstances, the substances, e.g. urine, are introduced into the pouch from the end of the sleeve that projects out from the bag. Thus, before reaching the inside of the bag, these substances flow against the wall of the sleeve. It is therefore necessary to ensure that this wall provides a degree of sealing.

One obvious solution would be to make the sleeve out of a tube having a closed outline that, in order to enable the pouch to pass into a flat configuration, would itself be flattened along two fold lines parallel to its longitudinal axis, thereby defining the longitudinal edges of the two walls of the flat sleeve that are situated facing each other. Nevertheless, that would require the sleeve to be fabricated initially as a three-dimensional shape and then flattened, which would increase production costs. Furthermore, in order to cause the sleeve to pass from its flat configuration to its channel configuration, the two opposite longitudinal edges of the flat sleeve are pressed towards each other. In order to ensure that this pressure deforms the two opposite walls so that they move apart from each other, it is desirable for these two walls initially to be slightly convex (seen from the outside). This leads to difficulties in terms of storing pouches before they are used since, if the walls of the flat sleeve need to remain somewhat convex, then the pouch is not perfectly flat and is therefore bulkier than a pouch that is genuinely flat.

It is also possible to imagine making the sleeve from two plane wall elements that are welded together along their facing longitudinal edges in order to have a closed outline. Under such circumstances, the welding itself presents a manufacturing step that increases production costs. Furthermore, starting from two plane elements that are welded together along their longitudinal edges, the chance of pressure applied to the longitudinal edges of the sleeve as formed in this way actually tending to shape the sleeve into a channel is only 50%. Such pressure serves either to make the two opposite walls convex, thereby making the desired channel, or else to make only one of the walls convex while the other wall adopts a concave shape and remains pressed against the convex wall. Under such circumstances, the channel does not form, and one-handed manipulation is unreliable.

The invention seeks to remedy the above-mentioned drawbacks by proposing a pouch having a sleeve that is very simple to fabricate and that can easily be manipulated in reliable manner, while nevertheless providing the degree of sealing desired in the portion of the sleeve that, in the utilization configuration, forms the channel for conveying waste to the inside of the pouch.

This object is achieved by the fact that the first wall of the sleeve presents a first longitudinal end strip projecting laterally from the edge of the opening, while the second wall presents a sliding edge suitable for sliding against the inside face of said first longitudinal strip when the pouch is passing from its flat configuration to its utilization configuration.

By virtue of these provisions, when the longitudinal edges of the sleeve are pressed towards each other, the first wall of the sleeve is certain to be deformed so as to become convex because of the fact that the first longitudinal end strip projects laterally relative to the edges of the opening. With this first wall made convex, the sliding edge of the second wall is constrained to slide against the inside face of the first longitudinal strip, which inside face is thus concave. Consequently, the second wall moves away from the first wall, such that together the two walls form between them the desired channel for holding the opening open. Furthermore, the sliding contact between the sliding edge and the second wall clearly provides a desired degree of sealing while the waste is being introduced into the pouch, thereby avoiding the waste leaking via the edge of the channel that has the sliding edge and the first longitudinal strip.

The pouch of the invention has numerous applications. The ease with which the sleeve can be manipulated in order to shape a channel is useful for all types of use. The improved way substances are conveyed along the channel into the pouch is useful in particular when the substances flow from members that cannot be inserted into the pouch. It is also useful when the substances flow from members that can be introduced into the pouch, since the invention makes it possible to avoid leaks without it being necessary to take particular care concerning the depth to which the members in question are introduced into the pouch.

Advantageously, the second wall of the sleeve presents a second longitudinal end strip projecting laterally from the edge of the opening, the sliding edge being formed on the second strip.

Under such circumstances, the pressure on the opposite longitudinal edges of the sleeve also deform the second wall directly in such a manner as to make it convex, the second longitudinal end strip being capable of sliding relative to the first via the sliding edge that is formed on the second strip and that slides against the inside face of the first strip.

It is nevertheless preferable for at least a portion of the first longitudinal strip to project laterally further than the second longitudinal strip relative to the edge of the opening.

Advantageously, the sliding edge is inclined, at least in an initial segment close to the opening, in the direction that increases the width of the second wall on going away from the opening. Thus, the base of the sliding edge adjacent to the opening may be practically in line with the edge of the opening, without projecting laterally relative to said edge, while the sliding edge moves away laterally from the edge of the opening as it moves away from the opening in the axial direction.

When it is desired to deform the initially flat sleeve in order to shape its walls into a channel, pressure is exerted on the opposite longitudinal edges of the sleeve in the vicinity of the base of the sleeve, i.e. in the region of the opening of the bag. The inclination of the sliding edge makes it possible to ensure that this pressure causes the sleeve to form a kind of cornet, deforming in particularly easy manner.

Advantageously, the second wall presents an outwardly-directed lateral step at the base of the sliding edge.

This upwardly-directed lateral step enables the base of the sliding edge to be held against the base of the first longitudinal end strip. While the sleeve is deforming, this thus avoids the two walls of the sleeve skewing relative to each other. This makes it more likely that the desired degree of sealing will be obtained. Furthermore, as can be seen below, this step helps to guide substances to the inside of the pouch.

Advantageously, the two walls are fastened together via their longitudinal edges respectively opposite from the first longitudinal strip and from the sliding edge.

In particular, the sleeve may be made from a flat blank that is folded in half via a fold line that forms a first longitudinal edge of the two walls of the sleeve.

Nevertheless, it is perfectly possible to make provision for the above-specified first longitudinal strip and sliding edge to be provided on both longitudinal edges of the sleeve. For example, the first wall of the sleeve may present a first longitudinal strip on each of its two opposite edges while the second wall presents a sliding edge (and possibly a second longitudinal strip) on each of its two opposite edges. It is also possible to make provision for the first wall to present a first longitudinal strip on one edge and a sliding edge on its other edge (possibly formed on a second longitudinal strip), and for the same to apply to the other wall.

Advantageously, the height by which the sleeve projects beyond the opening varies across the width of the sleeve between a minimum height measured in the vicinity of one of the lateral ends of the sleeve and a maximum height measured in the vicinity of the opposite lateral end.

Under such circumstances, and advantageously, the maximum height is measured in the vicinity of the lateral end of the sleeve where the first longitudinal end strip and the sliding edge are located.

With the present invention, a large degree of freedom is left for the shape of the free edge of the sleeve remote from the opening. This edge may be rectilinear, for example when the pouch is used as a urinal for male use. In other applications, for example when the pouch is used as a urinal for female use, it may be given a different shape. For example, by varying the height by which the sleeve projects, it is possible to adapt the free edge of the sleeve to female anatomy. This variation in height may be selected so that when the sleeve is shaped into a channel, the free edge of the channel can be pressed against the vulva of the woman using the pouch.

Advantageously, the pouch includes means for holding the walls of the sleeve in their channel-forming shape.

For example, the sleeve has two holder tongues carried respectively by the first and second walls of the sleeve on the side opposite from the opening of the pouch, each of the tongues presenting a free head that is separated from the wall that carries it by a blocking slot.

By this simple shape, when shaping the walls of the sleeve into a channel, it is possible to bring the tongue carried by the first wall of the sleeve to the inside of the tongue carried by the second wall, while conversely, the first longitudinal strip that is carried by the first wall is situated on the outside of the second wall. These two walls are thus held relative to each other.

Advantageously, the sleeve presents a segment inside the bag, which segment has spreader tabs formed in continuity respectively with each of the two walls of the sleeve and having free lateral ends suitable for spreading apart from each other in the utilization configuration of the pouch in order to space apart the opposite faces of the flexible bag.

Such spreader tabs are known from European patent application No. 0 847 742. They are compatible with the present invention, thus enabling a pouch to be made that combines the various above-mentioned advantages with reliable spreading apart of the sheets constituting the bag, even if those sheets are very flexible, and possibly initially likely stuck together.

It is also advantageous, in a region remote from the opening, for the bag to present a line of weakness suitable for being broken in order to form a tear that extends into the inside space of the bag.

The pouch can thus be emptied by manipulation that is simple.

The invention can be well understood and its advantages appear better on reading the following detailed description of an embodiment shown by way of non-limiting example. The description refers to the accompanying drawings, in which.

Figure 1:
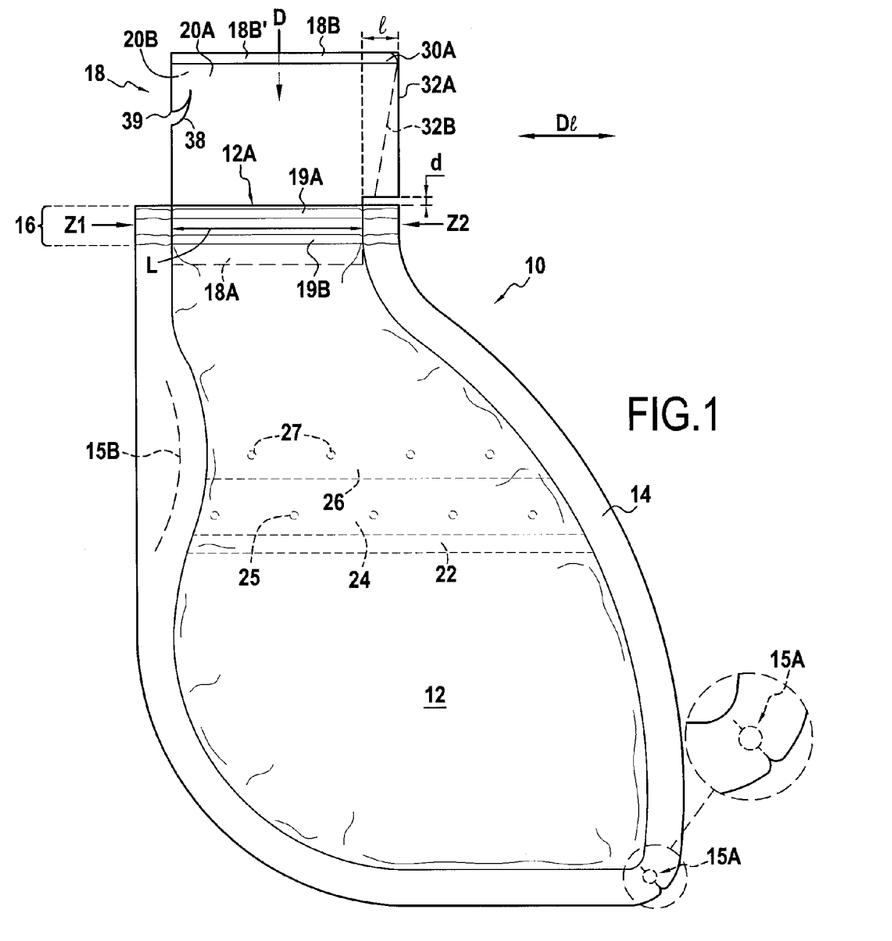
FIG. 1 is an elevation view of a pouch in accordance with the invention, in its flat configuration.

The pouch 10 shown in FIG. 1 comprises a flexible bag 12. In particular, the bag is made from two thin sheets of plastics material suitably cut out and welded together over practically their entire outline, by means of a weld line 14. The bag 12 has an opening 12A constituted by an interruption in the weld line 14 so as to enable the space inside the bag to communicate with the outside.

In the example shown, the opening is provided at the free end of a neck portion 16 presented by the bag, in which the bag is of reduced width.

The pouch has a reinforcing sleeve 18 that is fastened through the opening 12A and that projects to the outside of the bag.

Specifically, the sleeve comprises not only its main portion forming the sleeve proper, which portion projects beyond the opening 12, but also an internal portion 18A that is inserted in the opening so as to extend over the entire width L of the opening.

For example, the sheets that form the bag may be made of flexible plastics material, while the sleeve is made of stiffer plastics material. Thus, for the operation of fastening the sleeve to the bag, it suffices to weld or stick the sheets of the bag to the walls of the sleeve. Thus, in FIG. 1 there can be seen two weld lines given respective references 19A and 19B that extend transversely relative to the direction D along which waste is introduced into the pouch, with the front wall 20A of the sleeve that is visible in FIG. 1 being welded to the corresponding sheet of the bag along these lines. Naturally, the rear wall 20B of the sleeve is welded in the same manner to the opposite sheet of the pouch.

In FIG. 1, it can also be seen that in a region remote from the opening, the weld line 14 presents a line of weakness 15A, e.g. made with the help of a dotted line of microperforations. This weakness extends only over the line of welding without reaching the inside space of the bag. When the pouch is full of waste, the waste can thus be emptied out by tearing the bag along the line of weakness 15A, while using sufficient force to ensure that the resulting tear extends into the inside space of the bag.

Furthermore, on one of these sides adjacent to the opening, the line of welding 14 presents another line of weakness 15B that can likewise be constituted by discontinuous perforations. This line is at a distance from the inside space of the bag and it is oriented in such a manner that a tear along this line cannot propagate into the inside of the bag. Thus, when the pouch is full and it is desired to store it before emptying it, the line 15B may be torn in order to provide a slot enabling the pouch to be attached to a hook or the like.

FIG. 1 also shows that the pouch presents a safety valve of the type described in European patent application No. 0 847 742. Thus, the valve is constituted by a plurality of internal sheets arranged against each of the walls of the pouch. In the example shown, for each of the two walls of the pouch, the valve comprises a first pair of sheets 22 that extend from the opening 12A to a middle region of the pouch, a second pair of sheets 24 that extend inside the sheets of the first pair 22, and a third pair of sheets 26 that extend inside the second pair of sheets 24, the sheets 26 being shorter than the sheets 24 which are themselves shorter than the sheets 22. These sheets extend over the entire width of the pouch in the region in which they are located, and they are thus welded together and to the walls of the bag by the line of welding 14. The sheets of the pair 24 are also welded together by spot welds 25 and the sheets of the pairs 26 and 24 are welded together by spot welds 27 that are offset relative to the spot welds 25. These various pairs of suitably welded-together sheets constitute an anti-reflux check valve, preventing reflux of waste situated in the pouch when the pouch is handled after it has been used.

It can be seen that the line of weakness 15B lies in a region of the line of welding where all of the various layers of sheets are present, such that this line of welding is particularly strong, which enhances the above-mentioned attachment.

Figure 2:
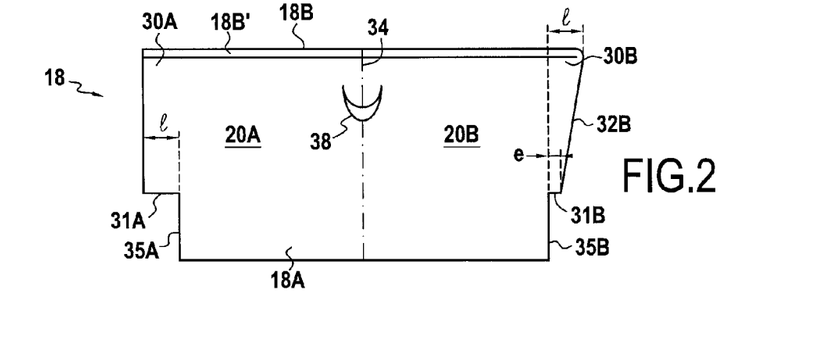
FIG. 2 is a plan view of the blank from which the sleeve of the FIG. 1 pouch is made.

The invention relates more particularly to the sleeve 18. As mentioned above, it is welded across the opening, with its internal portion 18A extending across the entire width L of the opening 12A. In FIG. 1 it can be seen that the front wall 20A of the sleeve, referred to below as the "first" wall, presents a first longitudinal end strip 30A that projects laterally from the edge of the opening 12A. In the meaning of the present patent application, the longitudinal direction is the direction D along which waste is introduced into the pouch, which direction is defined by the axis of the sleeve. The lateral direction Dl is thus perpendicular to the longitudinal direction. In FIG. 1 it can be seen that the first longitudinal strip 30A projects laterally by a width l from the edge of the opening. With reference to FIG. 2, it can be understood that the internal portion 18A of the sleeve is defined relative to the portion of the sleeve that projects outside the opening when the sleeve is in place in the pouch by a step 31A of width l.

For its part, the second wall 20B of the sleeve presents a sliding edge 32B that is suitable for sliding against the inside face of the first strip 30A when passing the pouch from its flat configuration to its utilization configuration.

Figure 3:
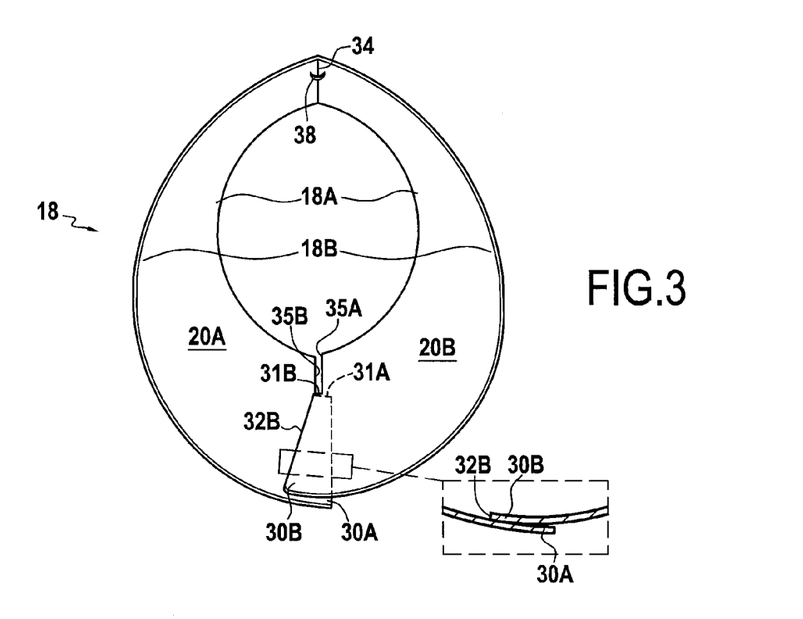
FIG. 3 is a perspective view showing the shape of the sleeve when the FIG. 1 pouch is in its utilization configuration.

FIG. 3 makes this phenomenon easy to understand since it shows the shape taken up by the sleeve while it is being shaped into a channel so as to cause the pouch to go from its flat configuration to its utilization configuration. In order to change the shape of the sleeve, the user exerts pressure in the zones Z1 and Z2 marked in FIG. 1 that are situated at the base of the sleeve. Under the effect of this pressure tending to move the opposite longitudinal edges of the sleeve towards each other, the walls of the sleeve become curved, with the first wall 20A adopting a convex shape while its longitudinal end strip, forming a free extension of this first wall, also adopts a convex shape, but with less curvature. Under the effect of the pressure exerted in the zones Z1 and Z2, the inside face of the first wall 20A exerts a reaction force against the free edge 32B and, because of the particular shape adopted by the first longitudinal strip 30A, the sliding edge is constrained to slide over this inside face in order to give the second wall 20B a convex shape. Thus, the two walls define between them the channel that causes the opening of the pouch to be maintained in an open situation.

Specifically, the sliding edge 32B is formed on the edge of a second longitudinal end strip 30B forming part of the second wall of the sleeve and projecting laterally relative to the edge of the opening. Over at least a segment, the strip 30B projects laterally to a smaller extent than the strip 30A. Specifically, the lateral projection of the strip 30B varies as a result of the sliding edge 32B being inclined. The maximum value of this lateral projection corresponds specifically to the width l of the first strip 30A, which width is constant in this example.

In FIG. 2 in particular it can be seen that the second wall 20B has an outwardly-directed lateral step 31B that is situated at the base of the sliding edge 32B, i.e. in the region of this sliding edge that is closest to the opening 12A of the pouch. This step 31B may be of very small width e, e.g. of the order of 5% to 20%, and preferably of the order of 10%, of the width l. Thus, the widths e and l may respectively be of the order of 1 millimeter (mm) to 2 mm, and of the order of 8 mm to 15 mm for pouches serving as urinals for human use.

As can be seen in FIGS. 2 and 3, the two walls 20A and 20B are fastened together via their longitudinal edges respectively opposite from the first longitudinal strip 30A and opposite from the sliding edge 32B. In the example shown, the sleeve 18 is made from a blank of plastics material that is folded along a fold line 34 so as to obtain the flat sleeve in the situation shown in FIG. 1. This fold line 34 forms the common longitudinal edges of the walls 20A and 20B that are connected together. Provision could also be made for the sleeve to be made up of two flat parts, i.e. in the form of two distinct blanks, that are welded together along their common line so as to form the fold line 34.

Thus, with the invention, the edges of the sleeve opposite from the line 34, i.e. the edges that are provided with the strip 30A and with the sliding edge 30B, are free to move relative to each other. This applies to all of the portion of the sleeve that projects beyond the opening 12A. Concerning the internal portion 18A of the sleeve, it is mentioned above that the width L of this internal portion in the flat configuration corresponds to the width of the opening 12A. Thus, for this internal portion, the edges 35A and 35B are incapable or practically incapable of moving relative to each other because of the presence of the line of welding 14. On the sides of the opening 12A, this line 14 may also encroach a little on the sleeve, i.e. on the portion of the fold line 34 that extends over the internal portion 18A of the sleeve and over the above-mentioned edges 35A and 35B.

In the example shown in FIGS. 1 to 3, the height over which the sleeve projects from the opening is substantially constant. Naturally, this does not prevent the top edge 18B of the sleeve 18 possibly being smoothed a little, if necessary. It may thus be chamfered or indeed it may be provided with a bead 18B'.

Figure 4:
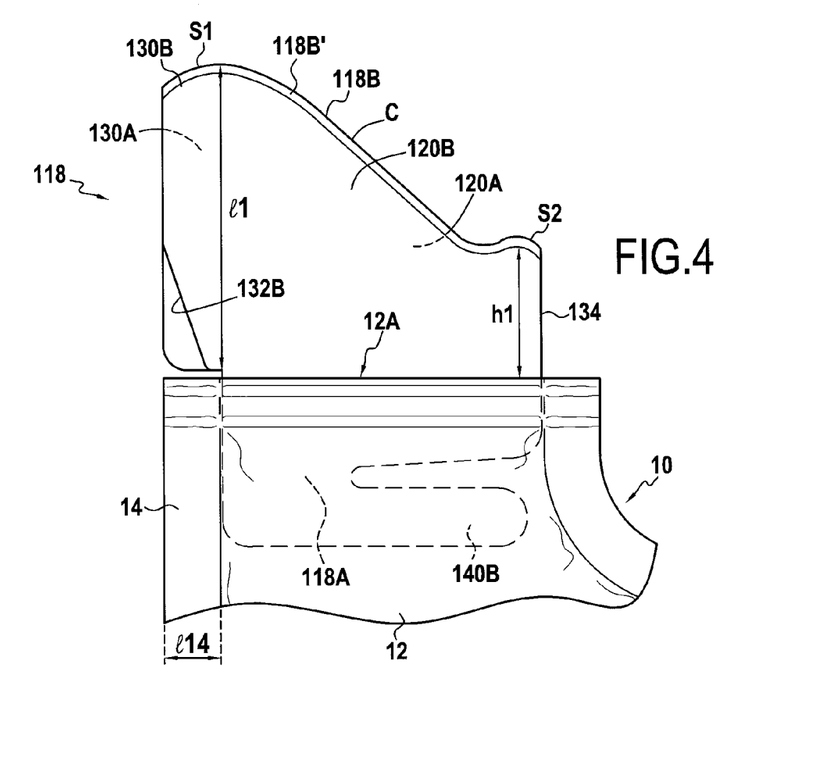
FIG. 4 is a view showing a portion of a pouch close to its opening in a variant embodiment that is particularly adapted for use as a female urinal.
Figure 5:
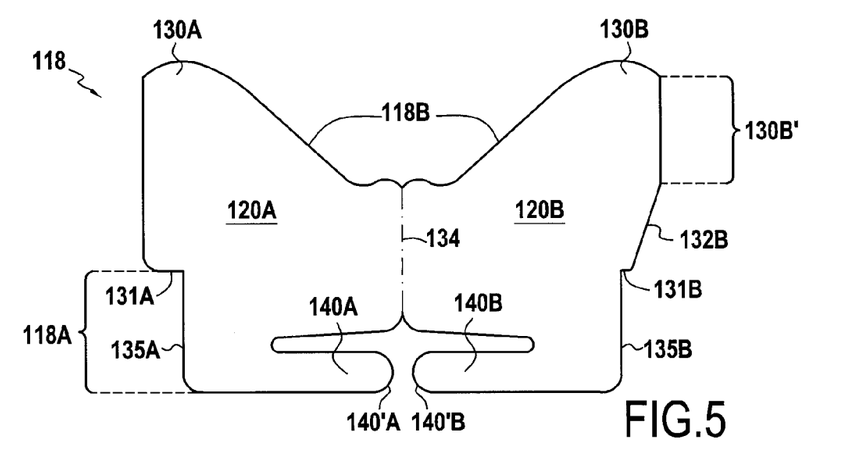
FIG. 5 is a plan view of the blank from which the sleeve of the FIG. 4 pouch is made.
Figure 6:
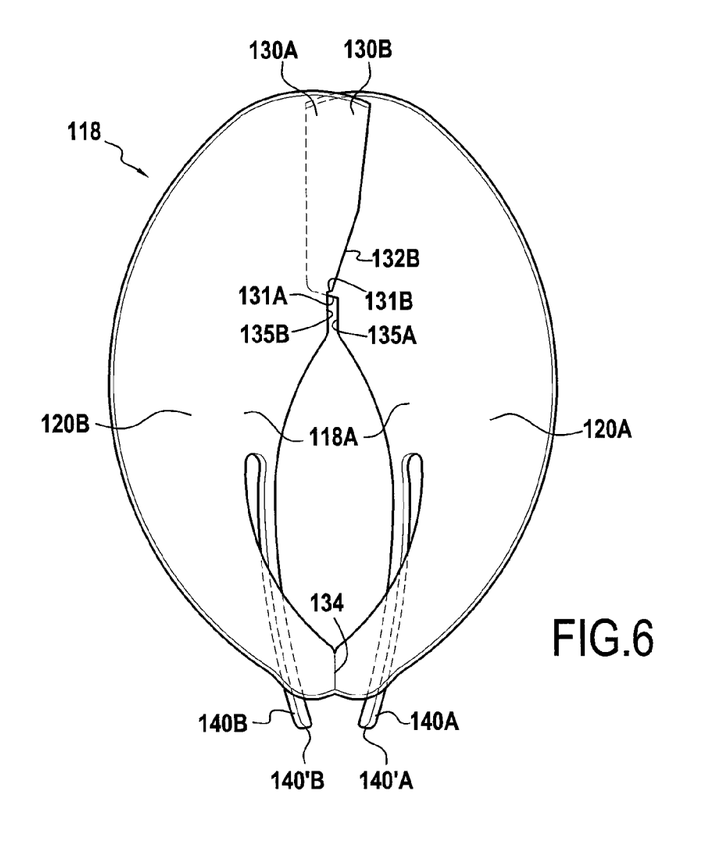
FIG. 6 is a perspective view showing the shape of the sleeve of the FIG. 4 pouch in the utilization configuration.

With reference to FIGS. 4 to 6, there follows a description of a variant embodiment of the sleeve. FIG. 4 shows only the portion of the pouch close to its opening 12A. The sleeve 118 is analogous to the above-described sleeve 18 but it differs therefrom in two aspects. Firstly, the free edge 118B of the sleeve 118 remote from the opening 12A has a particular shape, specifically a shape that is adapted for use as a female urinal. It is mentioned at this point that the free edge may present a bead or the like 118B' making it pleasant to the touch. Furthermore, the internal portion 118A of the sleeve presents spreader tabs that are described below.

The various elements constituting the sleeve 118 are given the same references as for the sleeve 18, plus 100. With reference to FIGS. 4 to 6, it can thus be seen that the sleeve 118 presents a first wall 120A and a second wall 120B that are connected together by a fold line 134. The first wall 120A presents a first longitudinal end strip 130A, while the second wall 120B presents a sliding edge 132B arranged on the edge of a second longitudinal strip 130B. In FIG. 4, it can be seen that the two longitudinal strips project laterally from the opening, i.e. that they project laterally relative to the lateral edge of the opening as defined by the line of welding 14. The first longitudinal strip 130A is generally situated in line with the line of welding 14 and presents a width that corresponds approximately to the width of the line of welding. The second longitudinal strip 130B presents a free terminal portion 130B' of substantially constant width, corresponding to the width 114 of the line of welding 14. Between the edge of the opening 12A and this terminal portion 130B', the second longitudinal end strip presents the sliding edge 132B that, like the sliding edge 32B in the above-described variant, is inclined in order to slide better against the inside face of the first longitudinal strip 130A. Steps 131A and 131B that are respectively analogous to the above-described steps 31A and 31B are situated at the bases of the longitudinal strips 130A and 130B.

As for the variant in the preceding figures, the variant of FIGS. 4 to 6 makes provision for the sleeve to be made from a folded blank. The two walls 120A and 120B are thus connected together by the fold line 134. In FIG. 4, it can be seen that the height that the sleeve 118 projects from the opening 12A varies along the width of the sleeve, between a minimum height h1 measured in the vicinity of one of the lateral ends of the sleeve, and a maximum height h2 measured in the vicinity of the other lateral end. Specifically, the maximum height h2 is measured in the vicinity of the lateral end of the sleeve at which the first longitudinal end strip 130A and the sliding edge 132B are located.

As can be seen in FIG. 4, when the pouch is in the flat configuration, the free edge 118B of the sleeve opposite from the opening 12A is substantially S-shaped with a central portion C in the form of a rising ramp, and two terminal portions given respective references S1 and S2 that are slightly rounded. This shape is particularly adapted for using the pouch as a female urinal. In order to use the pouch, it suffices to deform the sleeve in order to shape the channel and then to place the sleeve in such a manner that the shorter portion corresponding to the portion S2 is placed against the posterior portion of the vulva.

In the variant of FIGS. 4 to 6, the sleeve also presents spreader tabs. More precisely, the portion 118A of the sleeve that forms a segment thereof inside the bag 12 presents spreader tabs 140A and 140B. These tabs are formed respectively in continuity with each of the two walls of the sleeve and they have respective free lateral ends 140'A and 140'B that are suitable for spreading apart from each other in the utilization configuration of the pouch in order to space apart the opposite faces of the flexible bag, as described in European patent No. 0 847 742, and as can be understood by looking at FIG. 6.

The pouch of the invention advantageously has means for holding the walls of the sleeve in their channel-forming shape. For this purpose, it is possible for example to make a cutout in the sleeve of the same type as the cutout 38 shown in FIG. 2. This cutout is symmetrical relative to the fold line and has a smiley shape. Thus, above the cutout there is provided a tongue 39 that may be folded towards the inside or towards the outside of the sleeve in order to form a break in the fold line to oppose flattening of the sleeve.

Figure 7:
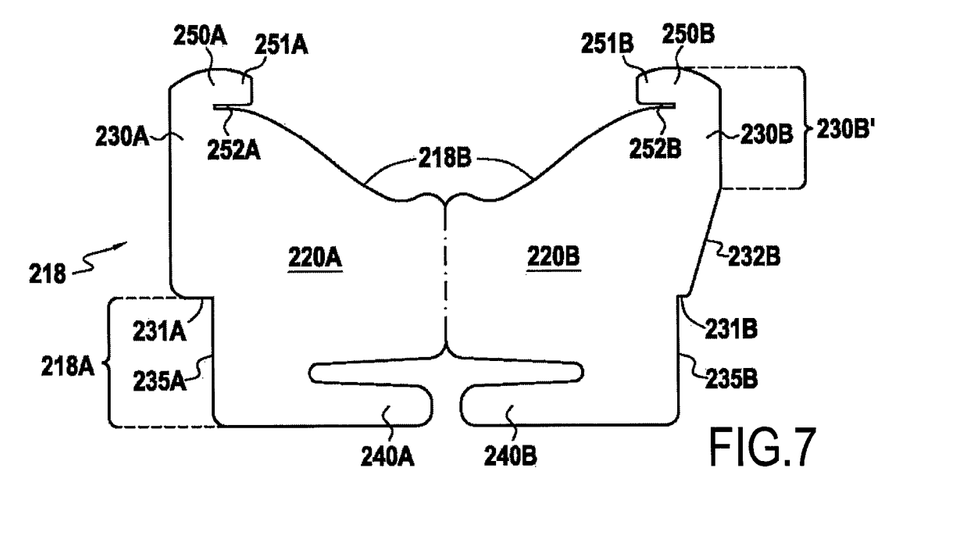
FIG. 7 is a plan view of the blank from which a sleeve is made in a variant embodiment.
Figure 8:
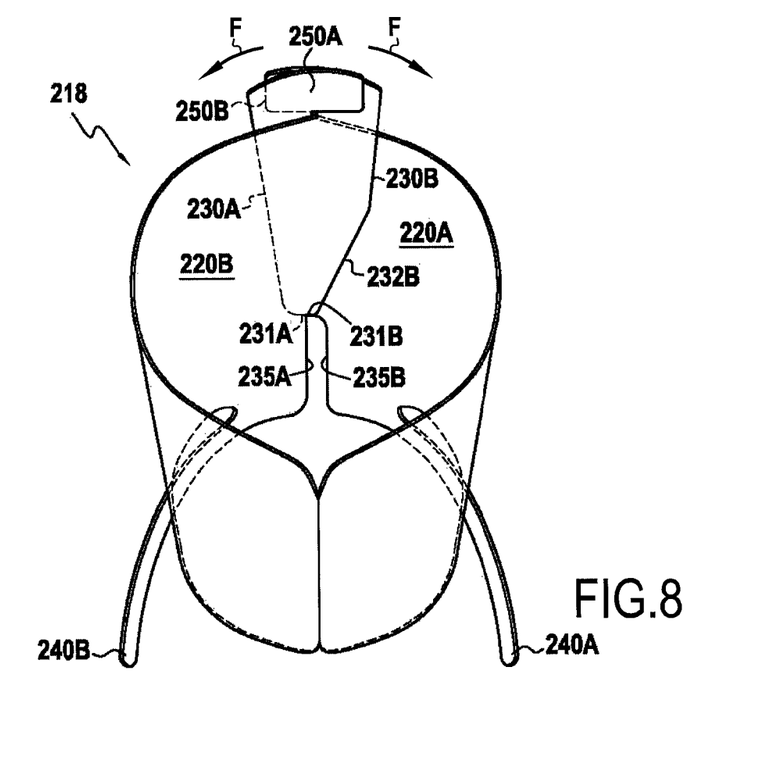
FIG. 8 is a perspective showing the sleeve of the FIG. 7 variant when the sleeve is shaped as a channel.

With reference to FIGS. 7 and 8, there follows a description of a variant embodiment of the sleeve, having means for holding the walls of the sleeve in their channel-forming shape, in another embodiment.

In FIGS. 7 and 8, the same references are used as in FIGS. 4 to 6, plus 100. The sleeve 218 shown in FIGS. 7 and 8 is analogous to the sleeve 118, and there can be seen in particular the two walls 220A and 220B, the longitudinal strips 230A and 230B, the sliding edge 232B, the lateral steps 231A and 231B, and the spreader tabs 240A and 240B.

Nevertheless, the sleeve 218 differs from the sleeve 118 in that it has two holder tongues 250A and 250B carried respectively by the first wall 220A and by the second wall 220B. Each of these tongues has a respective free head 251A, 251B that is spaced apart from the respective wall carrying it 220A, 220B by a respective slot 252A, 252B. These slots are generally oriented substantially transversely and they are oriented in such a manner that the free head 251A of the tongue 250A points away from the first longitudinal strip 230A, while the free head 251B of the tongue 250B points away from the sliding edge 232B.

Specifically, the portion of the tongue 250A attaching it to the first wall 220A lies substantially longitudinally in line with the first longitudinal strip 230A, and the portion of the tongue 250B attaching it to the second wall 220B lies substantially longitudinally in line with the second longitudinal strip 230B.

As can be seen in FIG. 8, when the sleeve is shaped as a channel, the slots 252A and 252B may be engaged one in the other. As mentioned above, in order to shape the sleeve into a channel, the sliding edge 232B has slid against the inside face of the first longitudinal strip 230A. Thus, as in all of the embodiments, the portion of the second wall adjacent to the sliding edge (this portion being the second longitudinal strip 30B, 130B, or 230B when present), is situated on the inside of the first wall of the sleeve when the sleeve is in its channel shape.

Because of the slots 252A and 252B interpenetrating, this situation is inverted for the tongues 250A and 250B. It is the first tongue 250A carried by the first wall 220A that is on the inside of the tongue 250B carried by the second wall 220B. As a result, each of the tongues is retained by the slot of the other tongue. Thus, the tongues are prevented from moving away from each other in the direction indicated by arrows F in FIG. 8, thereby ensuring that the sleeve is constrained to remain in its channel shape.

It is very simple to make the tongues 250A and 250B co-operate in this way. After shaping the sleeve into a channel, it suffices to take hold of them between two fingers and to cause them to slide one against the other until the tongue 250B passes behind the tongue 250A.

With reference to FIG. 8, it can also be seen that these superposed tongues provide a grip surface that can be pinched by the user in order to hold the sleeve in the appropriate position while the pouch is in use, in particular during micturition if the pouch is being used as a urinal.

Naturally, the holder tongues are entirely compatible with the variant embodiment of FIGS. 1 to 3 instead of and replacing the above-described cutout 38.

Whatever the variant used, the sleeve of the pouch of the invention presents the particular feature of passing very easily from its flat configuration to its channel configuration. Furthermore, although the sliding edge is free to slide relative to the first longitudinal strip, such that the sleeve is not welded in this zone, this sliding co-operation provides sealing. Firstly the sliding edge is in contact with the inside face of the first wall over its entire length and thus avoids unwanted leaks over all of this contact zone, and secondly the step 31B or 131B situated at the base of the sliding edge has the effect of guiding any liquid running along this edge towards the inside face of the wall 20B and thus towards the inside of the pouch. In the figures, it should be observed that the distance d between the top edge of the opening and the base of the longitudinal strip or the sliding edge (i.e. the base of the step 31A, 31B or 131A, 131B) is shown somewhat exaggerated. Specifically, the line of welding 119A is in fact made in such a manner as to extend almost as far as these bases. In this way, when liquid reaches the base of the sliding edge 32B, it is practically inside the bag.

Likewise, when the sleeve is shaped as a channel, the longitudinal edges of the inside portion of the sleeve (35A and 35B or 135A and 135B) touch each other, thereby contributing to the sealing effect. These edges are shown spaced apart in FIGS. 3 and 5 in order to clarify the drawing.

The invention claimed is:

1. A pouch comprising a flexible bag having an opening having an edge fastened to a first and a second opposite walls of a reinforcing sleeve projecting to the outside of the bag, the pouch being suitable for adopting a flat configuration in which said walls are situated one against the other, and a utilization configuration in which said walls form a channel that holds the opening open, the first wall presenting a first longitudinal end strip that projects laterally from the edge of the opening, while the second wall presents a sliding edge configured to slide against an inside face of said first longitudinal strip when the pouch is passing from its flat configuration to its utilization configuration.

2. A pouch as claimed in claim 1, wherein the second wall presents an outwardly-directed lateral step at the base of the sliding edge.

3. A pouch as claimed in claim 1, wherein the two walls are fastened together via their longitudinal edges respectively opposite from the first longitudinal strip and from the sliding edge.

4. A pouch as claimed in claim 1, wherein the sleeve presents a segment inside the bag, which segment has spreader tabs formed in continuity respectively with each of the two walls and having free lateral ends suitable for spreading apart from each other in the utilization configuration of the pouch in order to space apart the opposite faces of the flexible bag.

5. A pouch as claimed in claim 1, wherein, in a region remote from the opening, the bag presents a line of weakness suitable for being broken in order to form a tear that extends into the inside space of the bag.

6. A pouch as claimed in claim 1, wherein a height by which the sleeve projects beyond the opening varies across a width of the sleeve between a minimum height measured in the vicinity of one of the lateral ends of the sleeve and a maximum height measured in the vicinity of the opposite lateral end.

7. A pouch as claimed in claim 6, wherein the maximum height is measured in the vicinity of the lateral end of the sleeve where the first longitudinal end strip and the sliding edge are located.

8. A pouch as claimed in claim 6, wherein when the pouch is in the flat configuration, the free edge of the sleeve opposite from the opening represents an S-shape.

9. A pouch as claimed in claim 1, including means for holding the walls of the sleeve in their channel-forming shape.

10. A pouch as claimed in claim 1, wherein the sleeve has two holder tongues carried respectively by the first and second walls of the sleeve on the side opposite from the opening of the pouch, each of the tongues presenting a free head that is separated from the wall that carries said tongue by a blocking slot.

11. A pouch as claimed in claim 1, wherein the second wall presents a second longitudinal end strip that projects laterally from the edge of the opening, the sliding edge being formed on the second strip.

12. A pouch as claimed in claim 11, wherein the second wall presents an outwardly-directed lateral step at the base of the sliding edge.

13. A pouch as claimed in claim 11, wherein the sliding edge is inclined, at least in an initial segment close to the opening, in the direction that increases the width of the second wall on going away from the opening.

14. A pouch as claimed in claim 13, wherein the second wall presents an outwardly-directed lateral step at the base of the sliding edge.

* * * * *